United States Patent [19]

Newman

[11] Patent Number: 5,281,602

[45] Date of Patent: Jan. 25, 1994

[54] ANGIOTENSIN II RECEPTOR BLOCKING 2,3,6-SUBSTITUTED 5,6,7,8-TETRAHYDRO-PYRIDO[4,3-D]PYRIMIDIN-4(3H)-ONES

[75] Inventor: Howard Newman, Rockland, N.Y.

[73] Assignee: American Cyanamid Company, Wayne, N.J.

[21] Appl. No.: 52,933

[22] Filed: Apr. 23, 1993

[51] Int. Cl.$^5$ .................. C07D 487/04; A61K 31/505
[52] U.S. Cl. ..................................... 514/258; 544/279
[58] Field of Search ..................... 544/279; 514/258

[56] References Cited

U.S. PATENT DOCUMENTS 5,202,322  4/1993  Allen ..................... 514/228.2

FOREIGN PATENT DOCUMENTS 407342   6/1990  European Pat. Off. .
411766   6/1990  .
445811   3/1991  .
481448  10/1991  .
512870  11/1992  European Pat. Off. .
241257  12/1986  German Democratic Rep. .

*Primary Examiner*—Mark L. Berch
*Attorney, Agent, or Firm*—Thomas S. Szatkowski

[57] ABSTRACT

The invention provides novel 2,3,6-substituted 5,6,7,8-tetrahydro-pyrido[4,3-d]pyrimidin-4 (3H)-ones of the formula

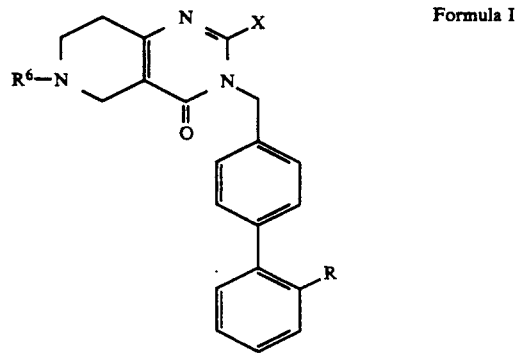

Formula I wherein X, R and $R^6$ are described in the specification which have activity as angiotensin II (AII) antagonists.

26 Claims, No Drawings

ANGIOTENSIN II RECEPTOR BLOCKING 2,3,6-SUBSTITUTED 5,6,7,8-TETRAHYDRO-PYRIDO[4,3-D]PYRIMIDIN-4(3H)-ONES

BACKGROUND OF THE INVENTION

1. Field of the Invention

This invention relates to certain novel 2,3,6-substituted 5,6,7,8-tetrahydro-pyrido[4,3-d]pyrimidin-4 (3H)-ones which have demonstrated activity as angiotensin II (AII) antagonists and are therefore useful in alleviating angiotensin induced hypertension and for treating congestive heart failure.

SUMMARY OF THE INVENTION

According to the present invention, there are provided novel compounds of Formula I which have angiotensin II-antagonizing properties and are useful as antihypertensives:

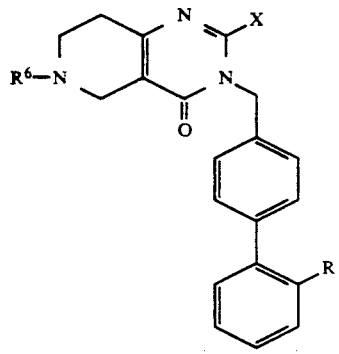

Formula I wherein:
R is

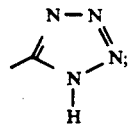

X is straight or branched alkyl of 3 to 5 carbon atoms;
$R^6$ is

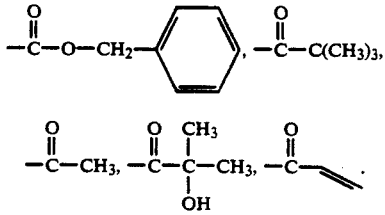

The present invention also provides novel intermediate compounds, methods for making the novel pyrimidin-4 (3H)-one angiotensin II antagonizing compounds, methods of using the novel pyrimidin-4 (3H)-one angiotensin II antagonizing compounds to treat hypertension, congestive heart failure and to antagonize the effects of angiotensin II.

SCHEME I

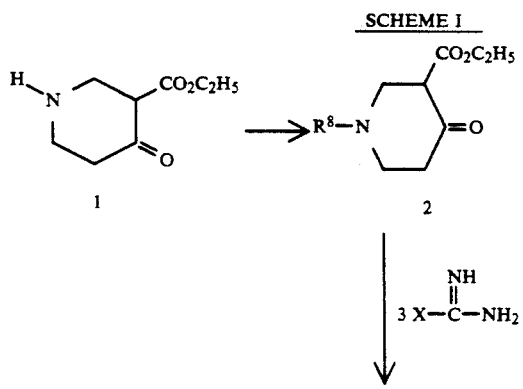

SCHEME I

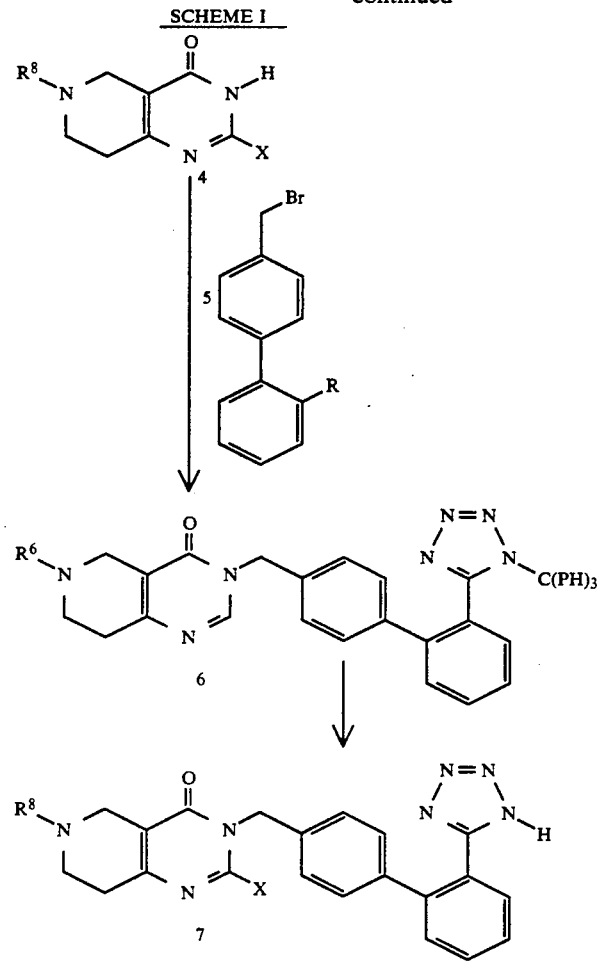

DETAILED DESCRIPTION OF THE INVENTION

The novel compounds of the present invention are prepared according to the following reaction schemes.

As illustrated in Scheme I, to prepare compounds for which $R^6$ is hereinbefore defined, 3-carbethoxy-4-piperidone hydrochloride 1, is acylated with benzylchloroformate, trimethylacetyl chloride or acetic anhydride in the presence of aqueous sodium carbonate to afford 2. In the case of 2-hydroxyisobutyric acid, acylation is accomplished in aqueous sodium carbonate using 1,1'-carbonyldiimidazole. Reaction of the acylated 1,3-dicarboxylate 2 with amidine 3 where x is hereinbefore defined in the presence of an alkoxide yields the appropriate 2-substituted-3,5,7,8-tetrahydro-4-oxo-pyrido[4,3-d]pyrimidine-6(4H)-carboxylate 4. The coupling of the pyrimidine intermediate 4 to the biphenyl tetrazole 5, where R is the trityl protected tetrazole is accomplished by dissolving the reactants in a suitable solvent such as N,N-dimethylformamide, N,N-dimethylacetamide, N-methylpyrrolidinone, methanol, ethanol, t-butanol, tetrahydrofuran, dioxane, acetone or dimethylsulfoxide in the presence of potassium carbonate or other suitable base such as sodium carbonate, cesium carbonate, sodium hydride, potassium hydride, sodium methoxide, sodium ethoxide, sodium t-butoxide, potassium t-butoxide or lithium methoxide for 2-24 hours, at 20°-80° C. to afford the alkylated pyrido[4,3-d]pyrimidin-4(3H)-one 6. Deprotection of the trityl group on 6 is accomplished by treatment with a catalytic amount of hydrochloric acid in acetone or other suitable acid such as sulfuric, trifluoroacetic or hydrogen chloride for 1-24 hours or by heating in tetrahydrofuran-methanol to afford the pyrido[4,3-d]pyrimidin-4(3H)-one 7.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitre or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation can be understood further by the following examples, but should not constitute a limitation thereof.

EXAMPLE 1

Methyl valerimidate hydrochloride

A solution of 16.5 g of valeronitrile and 9 ml of anhydrous methanol in 75 ml of isopropyl ether is cooled in ice and 8.02 g of gaseous HCl bubbled into the reaction mixture. The reaction mixture is refrigerated for 70 hours. A crystalline solid forms and is filtered, washed with isopropyl ether and dried under vacuum for 2 hours to afford 15.7 g of the desired product as a white crystalline solid, m.p. 81°–84° C.

EXAMPLE 2

Valeramidine hydrochloride

To 40 ml of anhydrous methyl alcohol is added 11.7 g of methyl valerimidate hydrochloride and the reaction mixture is cooled in ice while excess gaseous ammonia is added over 5 minutes. A colorless precipitate forms and is rapidly dissolved. The cooling bath is removed and the colorless solution kept at room temperature for 22 hours then evaporated. The concentrate is evaporated under high vacuum for 5 hours to afford 10.3 g of the desired product as a colorless oily solid.

EXAMPLE 3

1-(Phenylmethyl)-4-oxo-3-ethyl-1,3-piperidinedicarboxylic acid

To a mixture of 2.0 g of 3-carbethoxy-4-piperidone hydrochloride and 20 ml of 1M sodium carbonate is cooled in an ice bath and rapidly treated with 1.4 ml of benzylchloroformate. Stirring is continued in the cold for one hour. An opaque oil is formed and the reaction mixture is extracted with ether. The organic layer is dried with magnesium sulfate and concentrated to afford 3.0 g of a colorless oil.

EXAMPLE 4

Phenylmethyl 2-butyl-3,5,7,8-tetrahydro-4-oxo-pyrido[4,3-d]pyrimidine-6(4H)-carboxylate To a mixture of 3.0 g of 1-(phenylmethyl)-4-oxo-3-ethyl-1,3-piperidinedicarboxylic acid and 1.4 g of valeramidine hydrochloride is added 20 ml of dry ethanol followed by 10 ml of 1M sodium methoxide in methanol. The resulting mixture is stirred and heated under reflux for 1.5 hours. The reaction mixture is allowed to cool, filtered and the filtrate evaporated. The concentrate is stirred with 20 ml of ether for 20 minutes and the solid collected. The solid is air dried and then dried under vacuum at 56° C. for 1.5 hours to afford 2.3 g of a slightly tacky solid, m.p. 117°–122° C. The solid is stirred with water for 10 minutes and the solid collected, washed with water and air dried for 2 hours then at 56° C. under high vacuum for 1 hour to afford 1.9 g of colorless solid, m.p. 125°–127° C.

EXAMPLE 5

Phenylmethyl 2-butyl-3,5,7,8-tetrahydro-4-oxo-3-[[2'-[1-(triphenylmethyl)-1H-tetrazol-5-yl][1,1'-biphenyl]-4-yl]methyl-pyrido[4,3-d]pyrimidine-6(4H)-carboxylate To a stirred solution of 100 mg of phenylmethyl 2-butyl-3,5,7,8-tetrahydro-4-oxo-pyrido[4,3-d]-pyrimidine-6(4H)-carboxylate in 2 ml of dry N,N-dimethylformamide at room temperature is added 12 mg of 60% sodium hydride in mineral oil. After stirring at room temperature for 10 minutes, the clear, colorless solution is heated with 162 mg of 5-[4'-(bromomethyl)-[1,1'-biphenyl]-2-yl]-1-(triphenylmethyl)-1H-tetrazole. The resulting light yellow solution is stirred at room temperature for 17 hours and poured into cold water. The solid is collected by filtration washed with water and air dried for 2 hours to afford 0.25 g of product. The product is purified on thick layer silica gel plates by elution with 1:1 hexanes-ethyl acetate to afford 80 mg of the desired product as a colorless foam.

EXAMPLE 6

Phenylmethyl 2-butyl-3,5,7,8-tetrahydro-4-oxo-3-[[2'-[1-(triphenylmethyl)-1H-tetrazol-5-yl][1,1'-biphenyl]-4-yl]methyl-pyrido[4,3-d]pyrimidine-6(4H)-carboxylate To a stirred solution of 100 mg of phenylmethyl 2-butyl-3,5,7,8-tetrahydro-4-oxo-pyrido[4,3-d]-pyrimidine-6(4H)-carboxylate in 1 ml of dry methanol at room temperature is added 0.29 ml of 1M lithium methoxide in methanol. After stirring at room temperature for 1.5 hours the reaction mixture is evaporated and the residue dried under high vacuum for 18 hours. The residue is dissolved in 2 ml of dry tetrahydrofuran solution followed by 162 mg of 5-[4'-(bromomethyl)-[1,1'-biphenyl]-2-yl]-1-(triphenylmethyl)-1H-tetrazole. The resulting solution is stirred and heated under reflux for 48 hours then applied to thick layer silica gel plates. Elution with 1:1 hexanes-ethyl acetate affords 80 mg of the desired product as a colorless foam. The product is dissolved in acetone and while standing for a week crystals form.

EXAMPLE 7

Phenylmethyl 2-butyl-3,5,7,8-tetrahydro-4-oxo-3-[[2'-(1H-tetrazol-5-yl)[1,1'-biphenyl]-4-yl]methyl]pyrido[4,3-d]pyrimidin-6(4H)-carboxylate A solution of 80 mg of phenylmethyl 2-butyl-3,5,7,8-tetrahydro-3-[[2'-[1-(triphenylmethyl)-1H-tetrazol-5-yl][1,1'-biphenyl]-4-yl]methyl-pyrido-[4,3-d]pyrimidine-6(4H)-carboxylate in 2 ml of tetrahydrofuran is stirred at room temperature and treated with 1.0 ml of 3M hydrochloric acid. The resulting solution is stirred at room temperature for 1.5 hours and ice is added. The reaction mixture is made strongly basic with 0.4 ml of 10N sodium hydroxide. The turbid mixture is extracted with ether. The aqueous phase is acidified with hydrochloric acid and a gum separates. The aqueous phase is decanted and the gum washed with additional water. The gum is dissolved with methylene chloride, dried and evaporated to afford 20 mg of a colorless gum.

Ether is added to the gum followed by evaporation under vacuum to afford the desired product as a glass.

EXAMPLE 8

Ethyl 1-(2,2-dimethyl-1-oxopropyl)-4-oxo-3-piperidinecarboxylate

To a mixture of 2.0 g of 3-carbethoxy-4-piperidone hydrochloride and 20 ml of 1M sodium carbonate is cooled in an ice bath and rapidly treated with 1.3 ml of trimethylacetyl chloride. Stirring is continued in the cold for 1.5 hours. The reaction mixture is filtered and the collected solid washed with water, air dried and then dried at 56° C. for 1.25 hours under high vacuum to afford 1.4 g of the desired product as a colorless solid, m.p. 46°–50° C.

EXAMPLE 9

2-Butyl-6-(2,2-dimethyl-1-oxopropyl)-5,6,7,8-tetrahydro-pyrido[4,3-d]pyrimidin-4(3H)-one A mixture of 1.3 g of ethyl 1-(2,2-dimethyl-1-oxopropyl)-4-oxo-3-piperidinecarboxylate and 0.75 g of valeramidine hydrochloride in 10 ml of anhydrous ethyl alcohol is treated with 5.3 ml of a 1M solution of sodium methoxide in methanol. The resulting mixture is stirred and heated at reflux for one hour. The reaction mixture is allowed to cool over 30 minutes then filtered. The filtrate is evaporated to a gummy residue and stirred with 40 ml of ether for 30 minutes, filtered and the cake washed with ether. The cake is dried at 56° C. under vacuum to afford 1.0 g of the desired product as a colorless solid, m.p. 167°–172° C.

EXAMPLE 10

Ethyl 1-acetyl-4-oxo-3-piperidinecarboxylate

To a vigorously stirred, ice-water cooled suspension of 2.0 g of 3-carbethoxy-4-piperidone in 20 ml of aqueous sodium carbonate is added 1 ml of acetic anhydride. The mixture is stirred in the cold for 30 minutes then extracted with ether. The organic layer is dried and evaporated to afford 1.5 g of colorless solid, m.p. 53°–55° C.

EXAMPLE 11

6-Acetyl-2-butyl-5,6,7,8-tetrahydro-pyrido-[4,3-d]pyrimidin-4(3H)-one

A mixture of 1.5 g of ethyl 1-acetyl-4-oxo-3-piperidinecarboxylate and 1.0 g of valeramidine hydrochloride in 15 ml of anhydrous ethyl alcohol is treated with 7.5 ml of a 1M solution of sodium methoxide in methanol. The resulting mixture is stirred and heated at reflux for one hour. The reaction mixture is allowed to cool over 30 minutes then filtered. The filtrate is evaporated to a colorless syrup which is stirred with 50 ml of ether for 2 hours then filtered. The tacky cake is dried under high vacuum at 56° C. to afford 1.7 g of the desired product, m.p. 106°–113° C.

EXAMPLE 12

Ethyl 1-(2-hydroxy-2-methyl-1-oxopropyl)-4-oxo-3-piperidinecarboxylate

A suspension of 2.0 g of 3-carbethoxy-4-piperidone hydrochloride in 20 ml of 1M sodium carbonate is vigorously stirred at room temperature for 10 minutes then filtered. The filter cake is washed with a small amount of water, air dried followed by high vacuum drying at room temperature for 4 hours to afford 0.9 g of colorless solid, m.p. 125°–127° C. (compound A).

To an ice-bath cooled solution of 0.5 g of 2-hydroxyisobutyric acid in 5 ml of anhydrous tetrahydrofuran is added 0.8 g of 1,1'-carbonyldiimidazole. The cooling bath is removed immediately after adding the 1,1'-carbonyldiimidazole. After stirring for 15 minutes (compound A) is added in one portion with ice-water cooling. The cooling bath is removed and stirring continued for 18 hours. The reaction mixture is poured into ice-water and extracted with ether. The organic layer is dried and evaporated to afford 0.7 g the desired product as a colorless syrup.

EXAMPLE 13

2-Butyl-5,6,7,8-tetrahydro-6-(2-hydroxy-2-methyl-1-oxopropyl)-pyrido[4,3-d]pyrimidin-4(3H)-one A mixture of 0.7 g of ethyl 1-(2-hydroxy-2-methyl-1-oxopropyl)-4-oxo-3-piperidinecarboxylate and 0.4 g of valeramidine hydrochloride in 8 ml of anhydrous ethyl alcohol is treated with 2.8 ml of a 1M solution of sodium methoxide in methanol. The resulting mixture is stirred and heated at reflux for one hour. The reaction mixture is allowed to cool over 30 minutes then filtered. The filtrate is evaporated to a syrup which is stirred with 50 ml of ether overnight. The ether is decanted to afford a oily solid which is dissolved in acetone and applied to thick layer silica gel plates. The plates are eluted with ethyl acetate and the major zone washed stirred with water and the water decanted. The residue is dried and chromatographed on thick layer silica gel chromatography plates using ethyl acetate as the elution solvent. The major band at Rf=0.2 is isolated by washing with acetone to afford 0.65 g of the desired product as a colorless solid, m.p. 159°–161° C.

EXAMPLE 14

2-Butyl-5,6,7,8-tetrahydro-6-(2-hydroxy-2-methyl-1-oxo-propyl-3-[[2'-[1-(triphenylmethyl)-1H-tetrazol-5-yl][1,1'-biphenyl]-4-yl]methyl]-3-piperidinecarboxylate To a stirred mixture of 85 mg of 2-Butyl-5,6,7,8-tetrahydro-6-(2-hydroxy-2-methyl-1-oxo-propyl)-pyrido[4,3-d]pyrimidin-4(3H)-one in 2 ml of dry N,N-dimethylformamide at room temperature is added 12 mg of 60% sodium hydride in mineral oil. After stirring at room temperature for 10 minutes, the clear colorless solution is heated with 162 mg of 5-[4'-(bromomethyl)[1,1'-biphenyl]-2-yl]-1-(triphenylmethyl)-1H-tetrazole. The resulting light yellow solution is stirred at room temperature for 17 hours and poured into cold water. The resulting solid is collected, washed with water and dried under vacuum at 56° C. for one hour to afford 180 mg of colorless solid. The product is purified on thick-layer silica gel chromatography plates using 1:1 hexanes-ethyl acetate to afford 75 mg of the desired product as a colorless oil.

EXAMPLE 15

2-Butyl-5,6,7,8-tetrahydro-6-(2-hydroxy-2-methyl-1-oxopropyl-3-[[2'-[1-(triphenylmethyl)-1H-tetrazol-5-yl][1,1'-biphenyl]-4-yl]methyl]-3-piperidinecarboxylate To a stirred mixture of 255 mg of 2-Butyl-5,6,7,8-tetrahydro-6-(2-hydroxy-2-methyl-1-oxo-propyl)-pyrido[4,3-d]pyrimidin-4(3H)-one in 3 ml of dry methanol at room temperature is added 0.87 ml of 1M lithium methoxide in methanol. After stirring at room temperature for 1.5 hours the reaction mixture is evaporated to a residue which is dried under high vacuum for 18 hours. The residue is dissolved in 10 ml of dry tetrahydrofuran solution followed by the addition of 162 mg of 5-[4'-(bromomethyl)[1,1'-biphenyl]-2-yl]-1-(triphenylmethyl)-1H-tetrazole. The resulting solution is stirred and heated under reflux for 3 days and evaporated to approximately 2 ml and applied to thick layer silica gel plates. Elution with 1:1 acetone-hexanes affords 215 mg of the desired product as a pale yellow glass.

EXAMPLE 16

2-Butyl-5,6,7,8-tetrahydro-6-(2-hydroxy-2-methyl-1-oxopropyl)-3-[[2'-[1-(1H-tetrazol-5-yl)[1,1'-biphenyl]-4-yl]methyl]pyrido[4,3-d]pyrimidin-4(3H)-one A solution of 75 mg of 2-Butyl-5,6,7,8-tetrahydro-6-(2-hydroxy-2-methyl-1-oxopropyl)-3-[[2'-[1-(triphenylmethyl)-1H-tetrazol-5-yl][1,1'-biphenyl]-4-yl]methyl]-3-piperidinecarboxylate in 2 ml of tetrahydrofuran is stirred and 1 ml of 3N hydrochloric acid is added. Stirring is continued for 1 hour and 0.4 ml of 10N sodium hydroxide is added. The reaction mixture is extracted with ether. The aqueous layer is acidified with hydrochloric acid and extracted with methylene chloride. The organic layer is dried, evaporated and further dried under high vacuum to afford 34 mg of the desired compound as a glass.

Utility

The performance of the novel compounds of the present invention are shown in the following In Vitro test. The results of this test for representative compounds of the present invention are shown in Table I.

Angiotensin II Antagonists In Vitro Tests

Receptor Binding Assay:
Binding of [$^{125}$I] (Sar$^1$,Ile$^8$) AngII

The binding of [$^{125}$I] (Sar$^1$,Ile$^8$) AngII to microsomal membranes is initiated by the addition of reconstituted membranes (1:10 vols.) in freshly made 50.0 mMTris.HCl buffer, pH 7.4 containing 0.25% heat inactivated bovine serum albumin (BSA):80 ul membrane protein (10 to 20 ug/assay) to wells already containing 100 ul of incubation buffer (as described above) and 20 ul [$^{125}$I] (Sar$^1$,Ile$^8$) AngII (Specific Activity, 2200 Ci/mmole). Non-specific binding is measured in the presence of 1.0 uM unlabeled (Sar$^1$,Ile$^8$) AngII, added in 20 ul volume. Specific binding for [$^{125}$I] (Sar$^1$,Ile$^8$) AngII is greater than 90%. In competition studies, experimental compounds are diluted in dimethylsulfoxide (DMSO) and added in 20 ul to wells before the introduction of tissue membranes. This concentration of DMSO is found to have no negative effects on the binding of [$^{125}$I] (Sar$^1$,Ile$^8$) AngII to the membranes. Assays are performed in triplicate. The wells are left undisturbed for 60 min. at room temperature. Following incubation, all wells are harvested at once with a Brandel ® Harvester especially designed for a 96 well plate (Brandel ® Biomedical Research & Development Labs. Inc., Gaithersburg, Md., U.S.A.). The filter discs are washed with 10×1.0 ml of cold 0.9% NaCl to remove unbound ligand. Presoaking the filter sheet in 0.1% polyethylenemine in normal saline (PEI/Saline) greatly reduces the radioactivity retained by the filter blanks. This method is routinely used. The filters are removed from the filter grid and counted in a Parkard ® Cobra Gamma Counter for 1 min. (Packard Instrument Co., Downers Grove, Ill., U.S.A.). The binding data are analyzed by the non-linear interactive "LUNDON-1" program (LUNDON SOFTWARE Inc., Cleveland, Ohio U.S.A.). Compounds that displace 50% of the labelled angiotensin II at the screening dose of 50 μM are considered active compounds and are then evaluated in concentration-response experiments to determine their IC$_{50}$ values. The results are shown in Table I.

TABLE I

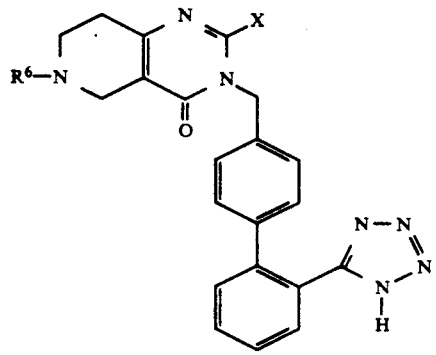

| Ex. No. | R$^6$ | X | Angiotension II Receptor Binding IC$_{50}$ (M) |
|---|---|---|---|
| 7 | phenyl-CH$_2$—O—C(=O)— | —(CH$_2$)$_3$CH$_3$ | 6.6 × 10$^{-7}$ |
| 16 | (CH$_3$)$_2$C(OH)—C(=O)— | —(CH$_2$)$_3$CH$_3$ | 6.0 × 10$^{-7}$ |

The enzyme renin acts on a blood plasma α$_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

The compounds of this invention inhibit the action of AII. By administering a compound of this invention to a rat, and then challenging with angiotensin II, a blockage of the vasopressor response is realized. The results of this test on representative compounds of this invention are shown in Table II.

AII Challenge

Conscious Male Okamoto-Aoki SHR, 16–20 weeks old, weighing approximately 330 g are purchased from Charles River Labs (Wilmington, Mass.). Conscious rats are restrained in a supine position with elastic tape. The area at the base of the tail is locally anesthetized by subcutaneous infiltration with 2% procaine. The ventral caudal artery and vein are isolated, and a cannula made of polyethylene (PE) 10–20 tubing (fused together by heat) is passed into the lower abdominal aorta and vena cava, respectively. The cannula is secured, heparinized (1,000 I.U./ml), sealed and the wound is closed. The animals are placed in plastic restraining cages in an upright position. The cannula is attached to a Statham P23Db pressure transducer, and pulsatile blood pressure is recorded to 10-15 minutes with a Gould Brush recorder. (Chan et al., (Drug Development Res., 18:75-94, 1989).

Angiotensin II (human sequence, Sigma Chem. Co., St. Louis, Mo.) of 0.05 and 0.1 ug/kg i.v. is injected into all rats (predosing response). Then a test compound, vehicle or a known angiotensin II antagonist is administered i.v., i.p. or orally to each set of rats. The two doses of angiotensin II are given to each rat again at 30, 90 and 150 minutes post dosing the compound or vehicle. The vasopressor response of angiotensin II is measured for the increase in systolic blood pressure in mmHg. The percentage of antagonism or blockade of the vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of

TABLE II

% INHIBITION (ANGIOTENSIN BLOCKAGE) OF ANGIOTENSIN II (A11) VASOPRESSOR RESPONSE

| Ex. No. | Dose (mg/kg) | A11 Dose mcg/kg IV | Min Post Dose | Control Before A11 | Response After A11 | Change | Average Change | % Inhibition |
|---|---|---|---|---|---|---|---|---|
| | | 0.05 | 0 | 190 | 230 | 40 | 37.5 | |
| | | | | 175 | 210 | 35 | | |
| | | 0.1 | | 185 | 230 | 45 | 42.5 | |
| | | | | 180 | 220 | 40 | | |
| 7 | 15 IV | 0.05 | 30 | 185 | 192 | 7 | 11 | 71 |
| | | | | 160 | 175 | 15 | | |
| | | 0.1 | | 175 | 190 | 15 | 17.5 | 59 |
| | | | | 160 | 180 | 20 | | |
| | | 0.05 | 60 | 170 | 200 | 30 | 25 | 33 |
| | | | | 170 | 190 | 20 | | |
| | | 0.1 | | 175 | 215 | 40 | 38 | 11 |
| | | | | 170 | 206 | 36 | | |
| | | 0.05 | 90 | 170 | 200 | 30 | 26 | 31 |
| | | | | 160 | 182 | 22 | | |
| | | 0.1 | | 170 | 210 | 40 | 42.5 | 0 |
| | | | | 155 | 200 | 45 | | |
| | 15 IV | 0.05 | 120 | 185 | 195 | 10 | 5 | 87 |
| | | | | 185 | 185 | 0 | | |
| | | 0.1 | | 170 | 176 | 6 | 8 | 81 |
| | | | | 170 | 180 | 10 | | |
| | | 0.05 | 180 | 175 | 200 | 25 | 25 | 33 |
| | | | | 135 | 160 | 25 | | |
| | | 0.1 | | 177 | 215 | 38 | 29 | 32 |
| | | | | 140 | 160 | 20 | | |
| | | 0.05 | 0 | 207 | 257 | 50 | 47 | |
| | | | | 185 | 225 | 40 | | |
| | | 0.1 | | 205 | 260 | 55 | 50 | |
| | | | | 185 | 230 | 45 | | |
| 16 | 15 IV | 0.05 | 30 | 195 | 210 | 15 | 12.5 | 72 |
| | | | | 175 | 185 | 10 | | |
| | | 0.1 | | 195 | 205 | 10 | 7.5 | 85 |
| | | | | 175 | 180 | 5 | | |
| | | 0.05 | 60 | 190 | 215 | 25 | 15 | 67 |
| | | | | 185 | 190 | 5 | | |
| | | 0.1 | | 190 | 220 | 30 | 21.5 | 57 |
| | | | | 175 | 188 | 13 | | |
| | | 0.05 | 90 | 183 | 225 | 42 | 28.5 | 37 |
| | | | | 175 | 190 | 15 | | |
| | | 0.1 | | 188 | 230 | 42 | 33.5 | 33 |
| | | | | 170 | 195 | 25 | | |
| | | 0.05 | 120 | 210 | 245 | 35 | 27.5 | 39 |
| | | | | 175 | 195 | 20 | | |
| | | 0.1 | | 200 | 240 | 40 | 32.5 | 35 |
| | | | | 175 | 200 | 25 | | |
| | | 0.05 | 180 | 175 | 230 | 55 | 42.5 | 6 |
| | | | | 165 | 195 | 30 | | |
| | | 0.1 | | 210 | 260 | 50 | 47.5 | 5 |
| | | | | 165 | 210 | 45 | | |

As can be seen from Tables I and II, the compounds demonstrate excellent Angiotensin II Receptor Binding activity as well as inhibiting the action of AII.

the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and anti-oxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compound is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

What is claimed is:

1. A pyrimidinone compound having the formula:

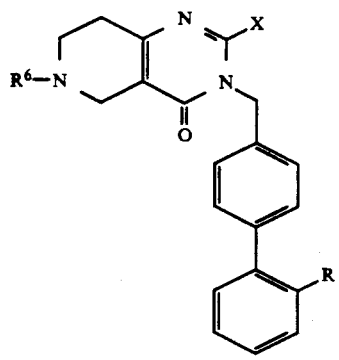

Formula I wherein:

R is

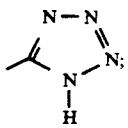

X is straight or branched alkyl of 3 to 5 carbon atoms;

$R^6$ is

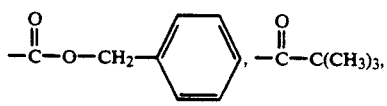

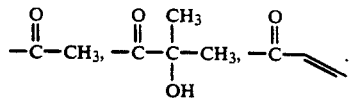

2. A method of antagonizing the effects of Angiotensin II in a mammal comprising administering a compound of claim 1 to said mammal in am amount effective to treat the effects of Angiotensin II.

3. The compound according to claim 1 wherein X is a straight chain alkyl of 3 or 4 carbon atoms; $R_6$ is

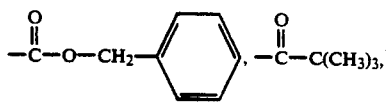

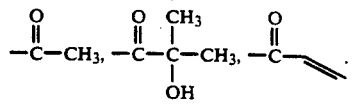

4. A pyrimidinone compound having the formula:

wherein:
X is straight or branched alkyl of 3 to 5 carbon atoms;
R⁶ is

−C(=O)−O−CH₂−C₆H₄−, −C(=O)−C(CH₃)₃,

−C(=O)−CH₃, −C(=O)−C(CH₃)(OH)−CH₃, −C(=O)−CH=CH₂.

5. The compound according to claim 4 wherein X is a straight chain alkyl of 3 or 4 carbon atoms; R₆ is

−C(=O)−O−CH₂−C₆H₄−, −C(=O)−C(CH₃)₃,

−C(=O)−CH₃, −C(=O)−C(CH₃)(OH)−CH₃, −C(=O)−CH=CH₂.

6. The compound according to claim 1 phenylmethyl 2-butyl-3,5,7,8-tetrahydro-4-oxo-3-[[2'-(1H-tetrazol-5-yl) [1,1'-biphenyl]-4-yl]methyl]-pyrido-[4,3-d]pyrimidin-6(4H)-carboxylate.

7. The compound according to claim 1 2-Butyl-5,6,7,8-tetrahydro-6-(2-hydroxy-2-methyl-1-oxopropyl)-3-[[2'-[1-(1H-tetrazol-5-yl) [1,1'-biphenyl]-4-yl]methyl]pyrido[4,3-d]pyrimidin-4(3H)-one.

8. The compound according to claim 1 2-butyl-6-(2,2-dimethyl-1-oxopropyl)-5,6,7,8-tetrahydro-3-[[2'-(1H-tetrazol-5-yl) [1,1'-biphenyl]-4-yl]methylpyrido[4,3-d]pyrimidin-4(3H)-one.

9. The compound according to claim 1 2-butyl-5,6,7,8-tetrahydro-6-(1-oxo-2-propenyl)-3-[[2'-(1H-tetrazol-5-yl) [1,1'-biphenyl]-4-yl]methyl-pyrido-[4,3-d]-pyrimidin-4(3H)-one.

10. The compound according to claim 1 6-acetyl-2-butyl-5,6,7,8-tetrahydro-3-[[2'-(1H-tetrazol-5-yl) [1,1'-biphenyl]-4-yl]-methyl]-pyrido[4,3-d]pyrimidin-4(3H)-one.

11. The compound according to claim 4 phenylmethyl 2-butyl-3,5,7,8-tetrahydro-4-oxo-3-[[2'-[1-(triphenylmethyl)-1H-tetrazol-5-yl][1,1'-biphenyl]-4-yl]methyl-pyrido[4,3-d]pyrimidine-6(4H)-carboxylate.

12. The compound according to claim 4 2-Butyl-5,6,7,8-tetrahydro-6-(2-hydroxy-2-methyl-1-oxo-propyl)-3-[[2'-[1-(triphenylmethyl)-1H-tetrazol-5-yl][1,1'-biphenyl]4-yl]methyl]-3-piperidinecarboxylate.

13. The compound according to claim 4 2-butyl-6-(2,2-dimethyl-1-oxopropyl)-5,6,7,8-tetrahydro-3-[[2'-[1-triphenylmethyl)-1H-tetrazol-5-yl]-[1,1'-biphenyl]-4-yl]methyl-pyrido[4,3-d]-pyrimidin-4-(3H)-one.

14. The compound according to claim 4 6-acetyl-2-butyl-5,6,7,8-tetrahydro-3-[[2'-[1-(triphenylmethyl)-1H-tetrazol-5-yl][1,1'-biphenyl]-4-yl]methyl-pyrido[4,3-d]pyrimidin-4(3H)-one.

15. The compound according to claim 4 2-butyl-5,6,7,8-tetrahydro-6-(1-oxo-2-propenyl)-3-[[2'-[1-(triphenylmethyl)-1H-tetrazol-5-yl][1,1'-biphenyl]-4-yl]methyl]-pyrido[4,3-d]-pyrimidin-4(3H)-one.

16. A pyrimidinone compound having the formula:

wherein:
X is a straight or branched alkyl of 3 to 5 carbon atoms;
R⁶ is

−C(=O)−O−CH₂−C₆H₄−, −C(=O)−C(CH₃)₃,

−C(=O)−CH₃, −C(=O)−C(CH₃)(OH)−CH₃, −C(=O)−CH=CH₂.

17. The compound according to claim 16 wherein X is a straight chain alkyl of 4 carbon atoms.

18. The compound according to claim 16 wherein X is a straight chain alkyl of 3 or 4 carbon atoms; R⁶ is

−C(=O)−O−CH₂−C₆H₄−, −C(=O)−C(CH₃)₃,

−C(=O)−CH₃, −C(=O)−C(CH₃)(OH)−CH₃, −C(=O)−CH=CH₂.

19. The compound according to claim 16 phenylmethyl 2-butyl-3,5,7,8-tetrahydro-4-oxopyrido[4,3-d]pyrimidine-6(4H)-carboxylate.

20. The compound according to claim 16 2-butyl-6-(2,2-dimethyl-1-oxopropyl)-5,6,7,8-tetrahydro-pyrido[4,3-d]pyrimidin-4(3H)-one.

21. The compound according to claim 16 6-Acetyl-2-butyl-5,6,7,8-tetrahydro-pyrido-[4,3-d]pyrimidin-4(3H)-one.

22. The compound according to claim 16 2-butyl-5,6,7,8-tetrahydro-6-(2-hydroxy-2-methyl-1-oxopropyl)-pyrido[4,3-d]pyrimidin-4(3H)-one.

23. The compound according to claim 16 2-butyl-5,6,7,8-tetrahydro-6-(1-oxo-2-propenyl)-pyrido-[4,3-d]pyrimidin-4(3H)-one.

24. A pharmaceutical composition useful for treating angiotensin induced hypertension or congestive heart failure in a mammal comprising a suitable pharmaceutical carrier and an effective amount of a compound of claim 1.

25. A method of treating angiotensin induced hypertension in a mammal comprising administering a compound of claim 1 to said mammal an amount effective to lower angiotensin induced hypertension.

26. A method of treating congestive heart failure in a mammal comprising administering a compound of claim 1 to said mammal in an amount effective to treat congestive heart failure.

* * * * *